United States Patent
Baeuchle et al.

(10) Patent No.: US 11,697,641 B2
(45) Date of Patent: Jul. 11, 2023

(54) IMPACT OF TRACE ELEMENTS IN THE GRIGNARD REACTION

(71) Applicant: BASF SE, Ludwigshafen am Rhein (DE)

(72) Inventors: Joerg Baeuchle, Grenzach-Wyhlen (DE); Wolfgang Wiesenhoefer, Grenzach-Wyhlen (DE)

(73) Assignee: BASF SE, Ludwigshafen am Rhein (DE)

( * ) Notice: Subject to any disclaimer, the term of this patent is extended or adjusted under 35 U.S.C. 154(b) by 93 days.

(21) Appl. No.: 17/442,862

(22) PCT Filed: Mar. 25, 2020

(86) PCT No.: PCT/EP2020/058327
§ 371 (c)(1),
(2) Date: Sep. 24, 2021

(87) PCT Pub. No.: WO2020/193617
PCT Pub. Date: Oct. 1, 2020

(65) Prior Publication Data
US 2022/0251050 A1   Aug. 11, 2022

(30) Foreign Application Priority Data
Mar. 27, 2019  (EP) .................... 19165605

(51) Int. Cl.
*C07D 251/20*   (2006.01)
(52) U.S. Cl.
CPC .................. *C07D 251/20* (2013.01)
(58) Field of Classification Search
CPC .................................... C07D 251/20
See application file for complete search history.

(56) References Cited

U.S. PATENT DOCUMENTS

| 5,955,060 A | 9/1999 | Huglin et al. |
| 2004/0258636 A1 | 12/2004 | Richard et al. |
| 2018/0170886 A1* | 6/2018 | Greiner .................. C07B 63/00 |

FOREIGN PATENT DOCUMENTS

EP   0775698 A1   5/1997

OTHER PUBLICATIONS

International Preliminary Report on Patentability received for PCT Patent Application No. PCT/EP2020/058327, dated Oct. 7, 2021, 7 pages.
International Search Report and Written Opinion received for PCT Patent Application No. PCT/EP2020/058327, dated May 18, 2020, 8 pages.
Lee et al., "Novel Orthogonal Synthesis of a Tagged Combinatorial Triazine Library via Grignard Reaction", Australian Journal of Chemistry: An International journal for chemical science, vol. 62, No. 9, Jan. 1, 2009, pp. 1000-1006.
Wang et al., "Synthesis, Spectra, and Theoretical Investigations of 1,3,5-Triazines Compounds as Ultraviolet Rays Absorber Based on Time-Dependent Density Functional Calculations and three-Dimensional Quantitative Structure-Property Relationship", Journal of Fluorescence, vol. 28, No. 2, May 2, 2018, pp. 707-723.

\* cited by examiner

*Primary Examiner* — Deepak R Rao
(74) *Attorney, Agent, or Firm* — Faegre Drinker Biddle & Reath LLP

(57) ABSTRACT

The present invention relates to an improved process for preparing 2,4-dichloro-6-(4-methoxyphenyl)-1,3,5-triazine (DICAT) comprising reacting 4-bromoanisole with magnesium, and reacting the resulting Grignard reagent with cyanuric chloride, wherein the magnesium comprises additional metals as impurities in an amount of less than 0.027% by weight, based on the total weight of the magnesium.

17 Claims, No Drawings

IMPACT OF TRACE ELEMENTS IN THE GRIGNARD REACTION

CROSS-REFERENCE TO RELATED APPLICATIONS

This application is a national stage application (under 35 U.S.C. § 371) of PCT/EP2020/058327, filed Mar. 25, 2020, which claims benefit of European Application No. 19165605.7, filed Mar. 27, 2019, both of which are incorporated herein by reference in their entirety.

The present invention relates to an improved process for preparing 2,4-dichloro-6-(4-methoxyphenyl)-1,3,5-triazine (DICAT) comprising reacting 4-bromoanisole with magnesium, and reacting the resulting Grignard reagent with cyanuric chloride, wherein the magnesium comprises additional metals as impurities in an amount of less than 0.027% by weight, based on the total weight of the magnesium.

DICAT is an intermediate compound for preparing DIOPAT which represents the starting material for the preparation of the UV absorber Tinosorb® S (also known as 2,2'-[6-(4-methoxyphenyl)-1,3,5-triazine-2,4-diyl]bis{5-[(2-ethylhexyl)oxy]phenol}, anisotriazine, bis-ethylhexyloxyphenol methoxyphenyl triazine, or bemotrizinol; CAS Number 187393-00-6) having the following chemical formula.

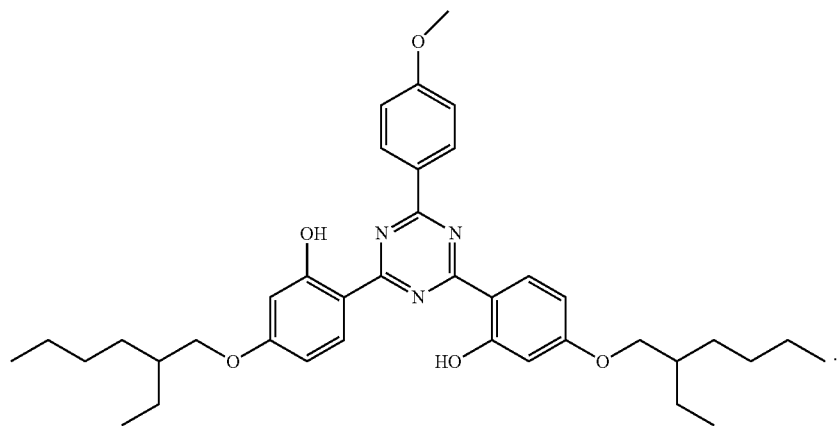

Tinosorb S

Tinosorb® S is a broad band UV absorber, absorbing UVB as well as UVA rays. Thus, Tinosorb® S is an important ingredient for sunscreen compositions and cosmetic applications.

One possible synthesis route to DIOPAT is performed via two steps, starting from 4-bromoanisole and cyanuric chloride under Grignard conditions to form the intermediate DICAT. In the second synthesis step, DICAT is reacted with resorcinol in a Friedel-Crafts reaction to form DIOPAT. In the following, the synthesis route to DIOPAT, starting from 4-bromoanisole and cyanuric chloride, is depicted, wherein the parameters a) Mg; b) cyanuric chloride; and c) resorcinol, $AlCl_3$ are typically applied.

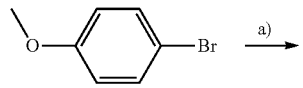

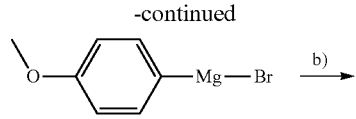

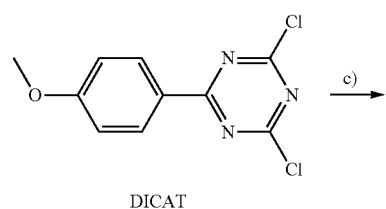

DICAT

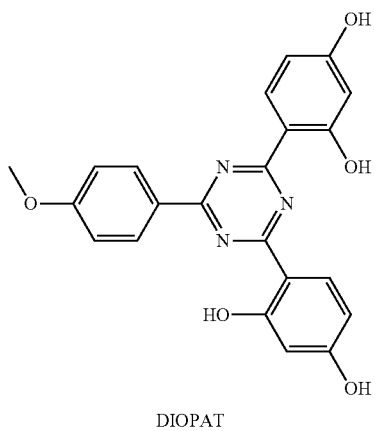

DIOPAT

To complete the synthesis to Tinosorb® S, a third step, the alkylation of DIOPAT with isooctyl chloride, is performed. In the following, the reaction to Tinosorb® S is depicted, wherein the parameters a) isooctyl chloride and a base are typically applied.

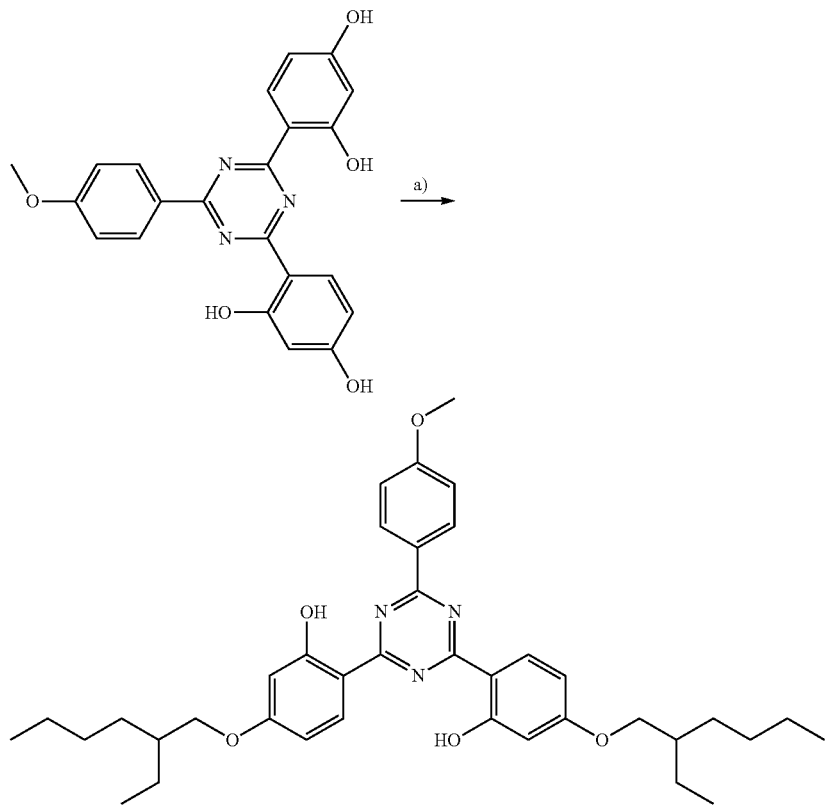

In connection with the preparation of DIOPAT, the process for preparing DICAT in step one of the synthesis causes difficulties. In particular, there is a need for improving the first step of reacting 4-bromoanisole with cyanuric chloride under Grignard conditions. The bromoanisole compound reacts with magnesium in an aprotic solvent to form the so-called Grignard reagent.

The Grignard reagent is a highly reactive organomagnesium compound. Due to the partially negatively charged carbon atom, the Grignard reagent is a versatile tool that can be used to form new carbon-carbon bonds. In the present case, the Grignard reagent undergoes a nucleophilic attack at the cyanuric chloride, so that the carbon atom attached to the Magnesium forms a bond with the hetaryl ring, thereby substituting the chloride atom.

However, the formation of by-products has been observed and the yields of the reaction are not satisfying for a commercial process.

Therefore, it was an object of the present invention to provide an improved process for preparing DICAT under Grignard conditions from 4-bromoanisole with cyanuric chloride.

It was a further object of the present invention to provide an improved process for preparing DICAT in high yields with less by-products.

It was another object of the present invention to provide an improved process with regard to safety and environmental conditions.

It has surprisingly been found that at least one of the above objects can be achieved by using magnesium of a certain quality in the preparation of DICAT via the Grignard route.

Therefore, the present invention relates to a process for preparing a compound of formula I

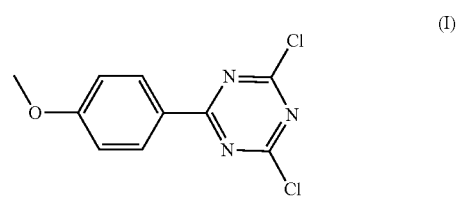 [SMILES: COc1ccc(-c2nc(Cl)nc(Cl)n2)cc1]

comprising the steps of
(i) reacting 4-bromoanisole with magnesium to obtain a Grignard reagent; and
(ii) reacting the Grignard reagent obtained in step (i) with a compound of formula (II)

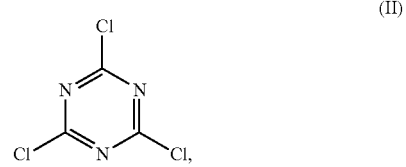

wherein the magnesium of step (i) comprises additional metals as impurities in an amount of less than 0.027% by weight, based on the total weight of the magnesium.

It has been found that, if the amount of additional metals in the magnesium is above 0.027% by weight, the yield of the Grignard reaction is negatively influenced and the formation of by-products is increased to a large extent. Therefore, a certain quality of the Grignard reagent as indicated above must be ensured. This is also advantageous for the safety of the reaction and the environment because the use of an excess of the Grignard reagent in comparison to the cyanuric chloride (compound of formula (II)) can be avoided.

It is to be understood that the reaction steps (i) and (ii) of the process of the present invention may be carried our separately, i.e. under isolation of the intermediate compounds, or without isolating the intermediate compounds. However, it is preferred that the reaction steps (i) and (ii) are carried out as a one-pot reaction, i.e. without isolation of the Grignard reagent.

In general, the reaction steps of the process of the invention as described in detail hereinafter are performed in reaction vessels customary for such reactions, the reactions being carried out in a continuous, semi-continuous or batchwise manner.

In general, the particular reactions will be carried out under atmospheric pressure. The reactions may, however, also be carried out under reduced pressure. It is preferred that the process of the invention, in particular the reaction steps (i) and (ii), are performed in a protective gas atmosphere, e.g. in a nitrogen atmosphere The temperatures and the duration times of the reactions may be varied in broad ranges, which the person skilled in the art knows from analogous reactions. The temperatures often depend on the reflux temperature of the solvents. Other reactions are preferably performed at room temperature, i.e. at about 25° C., or under ice cooling, i.e. at about 0° C. The end of the reaction can be monitored by methods known to a person skilled in the art, e.g. thin layer chromatography or HPLC.

If not otherwise indicated, the molar ratios of the reactants, which are used in the reactions, are in the range of from 0.2:1 to 1:0.2, preferably from 0.5:1 to 1:0.5, more preferably from 0.8:1 to 1:0.8. Preferably, equimolar amounts are used.

If not otherwise indicated, the reactants can in principle be contacted with one another in any desired sequence.

The person skilled in the art knows when the reactants or reagents are moisture sensitive, so that the reaction should be carried out under protective gases such as under a nitrogen atmosphere, and dried solvents should be used. Against this background, the process of the present invention, in particular the reaction steps (i) and (ii) are preferably carried out in a protective gas atmosphere, preferably under nitrogen.

The person skilled in the art also knows the best work-up of the reaction mixture after the end of the reaction.

In the following, preferred embodiments regarding the process of the invention are provided. It is to be understood that the preferred embodiments mentioned above and those still to be illustrated below are preferred alone as well as in combination with each other.

As indicated above, the present invention relates to a process for preparing a compound of formula I comprising the steps of
(i) reacting 4-bromoanisole with magnesium to obtain a Grignard reagent; and (ii) reacting the Grignard reagent obtained in step (i) with a compound of formula (II)

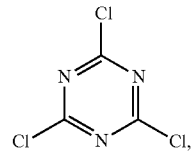

(II)

wherein the magnesium of step (i) comprises additional metals as impurities in an amount of less than 0.027% by weight, based on the total weight of the magnesium.

4-Bromoanisole, also known as para-bromoanisole or 1-bromo-4-methoxybenzene, has the following structure:

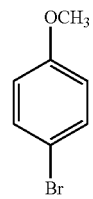

Without being bound to theory, in step (i) of the reaction, a Grignard reagent is formed by insertion of a magnesium atom into the carbon-bromine bond of the 4-bromoanisole. In the Grignard reagent the carbon atom of the former carbon-bromine bond has been made nucleophilic, so that it will easily react with the compound of formula (II) in step (ii), so as to form the desired compound of formula (I). As a byproduct, salts of magnesium with bromide and/or chloride will typically be obtained.

For the formation of the Grignard reagent, it seems to be highly advantageous, if the magnesium does not comprise any metal impurities in a significant amount. As used herein, the term "magnesium" refers to the magnesium as available, which has a certain content of magnesium as intended, but typically also comprises impurities, e.g. additional metals. It is preferred that the amount of impurities is as low as possible.

As indicated above, the magnesium preferably comprises additional metals as impurities in an amount of less than 0.027% by weight, based on the total weight of the magnesium. In this regard, the amount of less than 0.027% by weight refers to the overall amount of additional metals, if more than one additional metal is present. In a preferred embodiment, the magnesium comprises the additional metals in an amount of less than 0.02% by weight, based on the total weight of the magnesium. Again, the amount of less than 0.02% by weight refers to the overall amount of additional metals, if more than one additional metal is present. In a more preferred embodiment, the magnesium comprises the additional metals in an amount of less than 0.015% by weight, based on the total weight of the magnesium. Again, the amount of less than 0.015% by weight refers to the overall amount of additional metals, if more than one additional metal is present.

In particular, it is preferred that the amount of aluminum, manganese, silicon, iron, copper, and calcium should be as low as possible. Thus, in a preferred embodiment, the additional metals mentioned above as impurities in the magnesium being present in an overall amount of less than 0.027% by weight, preferably less than 0.02% by weight, more preferably less than 0.015% are preferably selected from aluminum, manganese, silicon, iron, copper, and calcium. Again, the amounts in weight-% refer to the overall amount of additional metals, if more than one additional metal is present.

Regarding the individual metals, the following threshold values are preferred alone as well as in combination.

In one preferred embodiment, the magnesium comprises aluminum as an impurity in an amount of less than 0.008%, based on the total weight of the magnesium.

In another preferred embodiment, the magnesium comprises manganese as an impurity in an amount of less than 0.004%, based on the total weight of the magnesium.

In yet another preferred embodiment, the magnesium comprises silicon as an impurity in an amount of less than 0.006%, based on the total weight of the magnesium.

In yet another preferred embodiment, the magnesium comprises iron as an impurity in an amount of less than 0.003%, based on the total weight of the magnesium.

In yet another preferred embodiment, the magnesium comprises copper as an impurity in an amount of less than 0.003%, based on the total weight of the magnesium.

In yet another preferred embodiment, the magnesium comprises calcium as an impurity in an amount of less than 0.003%, based on the total weight of the magnesium.

A skilled person is aware of suitable methods for performing a trace analysis of metals in materials including colorimetry and atomic spectroscopy. Atomic spectroscopy has become a major tool in this regard, where inductively coupled plasma atomic emission spectrometry (ICP-AES) and atomic absorption spectrometry (AAS) are widely used as methods. They observe atomic spectra on measurement, which are generated in ultraviolet and visible region due to radiative transitions of outer orbital electrons between the ground state and excited state of an atom. The spectra are elementally specific and their signal intensities relate to the concentrations of the elements, thus allowing selective qualification and quantification. In general, obtainable spectra in the atomic spectroscopy can be classified into three categories: (a) spontaneous emission from a higher excited state to a lower state; (b) absorption of radiation corresponding with a transition from a lower state to a higher state; and (c) induced resonant emission for the transition from a higher state to a lower state just after the absorption of external distinctive radiation. ICP-AES utilizes spectra of type (a) because high temperatures of 5000-6000 K generated in argon ICP bring almost all the atoms in a higher excited state. AAS utilizes the ones of type (b) because flames generated with acetylene premixed with air or nitrous oxide and electrical furnaces, which are typically suitable as excitation sources for AAS, can reach relatively low temperatures in the region of 2000-3000 K only to bring them in a lower state.

The magnesium itself, i.e. the pure magnesium not taking into account the above-mentioned impurities, may partly be present in oxidized form, i.e. as magnesium oxide instead of in the form of metallic magnesium. It is preferred that the amount of metallic magnesium is as high as possible, while the amount of magnesium oxide is as low as possible. As used herein, "metallic magnesium" refers to pure magnesium in non-oxidized form. As used herein, "magnesium oxide" refers to pure magnesium in oxidized form. The amounts of metallic magnesium and magnesium oxide are given relative to the amount of the pure magnesium hereinafter, i.e. the magnesium without the metal impurities.

In a preferred embodiment, the magnesium comprises magnesium oxide in an amount of less than 0.35% by weight, based on the total weight of the pure magnesium. Preferably, the magnesium comprises magnesium oxide in an amount of less than 0.25% by weight, more preferably less than 0.15% by weight, based on the total weight of the pure magnesium.

In general, it is preferred that the metallic magnesium content of the magnesium is as high as possible. Therefore, in a preferred embodiment, the magnesium comprises metallic magnesium in an amount of more than 99.6% by weight, based on the total weight of the pure magnesium. Particularly preferably, the magnesium comprises metallic magnesium in an amount of at least 99.65% by weight, based on the total weight of the pure magnesium.

The magnesium may be provided in any suitable form, wherein a high surface is desired. In a preferred embodiment, the magnesium is provided in the form of shavings, powder or flakes.

A skilled person is aware of suitable solvents for the formation of a Grignard reagent and a subsequent reaction thereof. As the reaction steps (i) and (ii) of the process of the present invention are preferably performed as a one-pot reaction, i.e. without isolation of the Grignard reagent, the solvent is preferably identical for both reaction steps.

In a preferred embodiment, the solvent of step (i) and/or step (ii) is an aprotic solvent, preferably an ether or amine solvent, wherein the solvent is particularly preferably selected from the group consisting of diethylether, tetrahydrofuran, trimethylamine and 1,4-dioxane.

In a more preferred embodiment, solvent is diethylether or tetrahydrofuran.

Mild reaction conditions are preferred for the process of the present invention. For the reaction step (ii), it is typically required to cool the reaction mixture, as the reaction is exothermic. Furthermore, the reactions are typically carried out under atmospheric pressure.

In a preferred embodiment, the reaction temperature of step (i) is in the range of from 35° C. to 80° C., preferably in the range of from 40° C. to 75° C.

In another preferred embodiment, the reaction temperature of step (ii) is in the range of from 0° C. to 15° C., preferably in the range of from 2° C. to 10° C.

The reaction times may very over a broad range. Preferred reaction times are in the range of from 1 hour to 12 hours, preferably in the range of from 3 hours to 6 hours, e.g. 4 or 5 hours.

A skilled person is aware, in which order the reactants are added for performing the reactions of the process of the invention. For the preparation of the Grignard reagent it is preferred that the magnesium is provided in a solvent, and the 4-bromoanisole is then added. For the subsequent reaction it is preferred that the compound of formula (II) is provided in a solvent, and then the Grignard reagent is added.

In a preferred embodiment, in step (i), the 4-bromoanisole is added to the magnesium, wherein the magnesium is provided in a solvent as defined above, and in step (ii) the Grignard reagent obtained in step (i) is added to the compound of formula (II), wherein the compound of formula (II) is provided in a solvent as defined above.

The skilled person is aware that it can be preferred that the addition of one reactant to the other may be performed continuously or stepwise, especially if the reaction is exothermic, so that the reaction temperature needs to be controlled.

It is preferred that the reactants are not used in a large excess, but rather that equimolar amounts are used.

In a preferred embodiment, in step (i), 4-bromoanisole and magnesium are reacted with each other in a molar ratio of from 1.2:1 to 1:1.2, and/or in step (ii), the Grignard reagent obtained in step (i) is reacted with the compound of formula (II) in a molar ratio of from 1.2:1 to 1:1.2.

Particularly preferred are molar ratios of from 1.1:1 to 1:1.1 for reaction step (i) and molar ratios of from 1.1:1 to 1:1.1 for reaction step (ii). Especially preferred is a molar ratio of 1:1 for both, reaction step (i) and reaction step (ii).

The process according to the present invention provides the compound of formula I in a high yield. In a preferred embodiment, the compound of formula I is obtained in a yield of at least 95%.

The process of the present invention may comprise further reaction steps in order to prepare Tinosorb® S.

In a preferred embodiment, the process therefore further comprises reacting the compound of formula (I) with resorcinol in the presence of AlCl₃ to obtain a compound of formula (III)

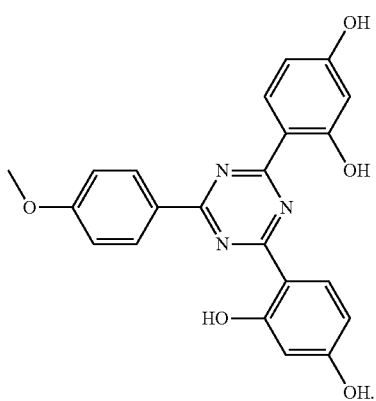

(III)

In a more preferred embodiment, the process further comprises reacting the compound of formula (III) with isooctyl chloride in the presence of a base to obtain a compound of formula (IV)

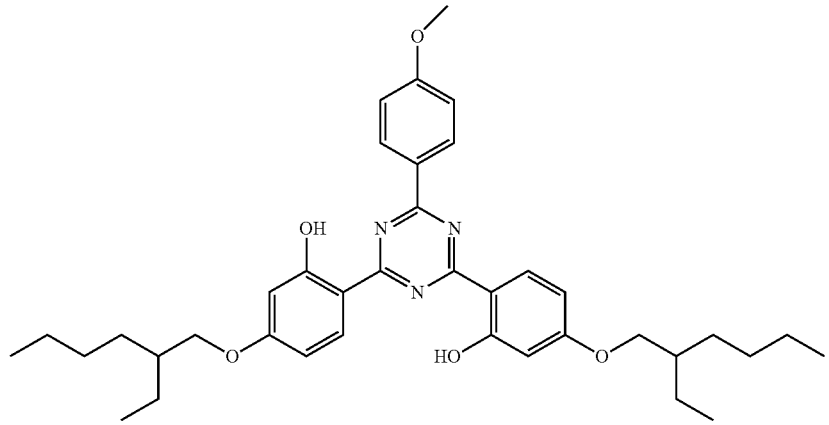

(IV)

The skilled person is aware of suitable reaction conditions for the Friedel-Crafts reaction as well as the alkylation reaction to obtain the compound of formula (IV), i.e. Tinosorb® S.

The present invention is further illustrated by the following examples.

EXAMPLES

Example 1

General Procedure for the Preparation of 2,4-dichloro-6-(4-methoxyphenyl)-1,3,5-triazine (DICAT)

In a first reaction vessel, 1.0 mol magnesium was added to 2.5 mol tetrahydrofuran. The mixture was heated to 45° C. Then, 1.0 mol 4-bromoanisole was added at a temperature of about 70° C. The reaction mixture was allowed to cool to room temperature. In a second reaction vessel, 12.7 mol tetrahydrofuran was provided. 1.0 mol cyanuric chloride was added. At a temperature of about 7° C., the Grignard reagent obtained in the first reaction vessel was added to the mixture in the second reaction vessel. The reaction was completed after 2 hours. The solvent was removed.

The following table provides the yields of DICAT, if magnesium is used, which comprises additional metals as impurities in an amount of less than 0.027% by weight, based on the total weight of the magnesium:

| No. | Met. Mg [%] | Al [%] | Mn [%] | Si [%] | Fe [%] | Cu [%] | Ca [%] | Mg [%] | MgO [%] | Yield [%] |
|---|---|---|---|---|---|---|---|---|---|---|
| 1 | 99.7 | 0.0048 | 0.0038 | 0.0047 | 0.0029 | 0.0004 | 0.0003 | 99.98 | 0.12 | 96 |
| 2 | 99.7 | 0.0043 | 0.0072 | 0.0028 | 0.0025 | 0.0004 | 0.0001 | 99.98 | 0.05 | 94.6 |
| 3 | 99.7 | 0.0011 | 0.0039 | 0.0043 | 0.0024 | 0.0001 | 0.0016 | 99.99 | 0.05 | 95.2 |

The invention claimed is:

1. A process for preparing a compound of formula I

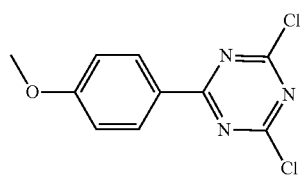

comprising the steps of
(i) reacting 4-bromoanisole with magnesium to obtain a Grignard reagent; and
(ii) reacting the Grignard reagent obtained in step (i) with a compound of formula (II)

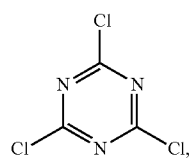

wherein the magnesium of step (i) comprises additional metals as impurities in an amount of less than 0.027% by weight, based on the total weight of the magnesium.

2. The process according to claim 1, wherein the magnesium comprises the additional metals in an amount of less than 0.02% by weight, based on the total weight of the magnesium.

3. The process according to claim 1, wherein the additional metals are selected from the group consisting of aluminum, manganese, silicon, iron, copper and calcium.

4. The process according to claim 1, wherein the magnesium comprises magnesium oxide in an amount of less than 0.35% by weight, based on the total weight of the pure magnesium.

5. The process according to claim 1, wherein the magnesium comprises metallic magnesium in an amount of more than 99.6% by weight, based on the total weight of the pure magnesium.

6. The process according to claim 1, wherein the magnesium is provided in the form of shavings, powder or flakes.

7. The process according to claim 1, wherein the compound of formula I is obtained in a yield of at least 95%.

8. The process according to claim 1, wherein the solvent of one or both of step (i) and step (ii) is an aprotic solvent.

9. The process according to claim 1, wherein the solvent is diethylether or tetrahydrofuran.

10. The process according to claim 1, wherein the reaction temperature of step (i) is in the range of from 35° C. to 80° C.

11. The process according to claim 1, wherein the reaction temperature of step (ii) is in the range of from 0° C. to 15° C.

12. The process according to claim 1, wherein in step (i) the 4-bromoanisole is added to the magnesium, wherein the magnesium is provided in a solvent according to claim 8, and in step (ii) the Grignard reagent obtained in step (i) is added to the compound of formula (II), wherein the compound of formula (II) is provided in a solvent according to claim 8.

13. The process according to claim 1, wherein in step (i) 4-bromoanisole and magnesium are reacted with each other in a molar ratio of from 1.2:1 to 1:1.2, or wherein in step (ii) the Grignard reagent obtained in step (i) is reacted with the compound of formula (II) in a molar ratio of from 1.2:1 to 1:1.2.

14. The process according to claim 1, wherein the process further comprises reacting the compound of formula (I) with resorcinol in the presence of AlCl₃ to obtain a compound of formula (III)

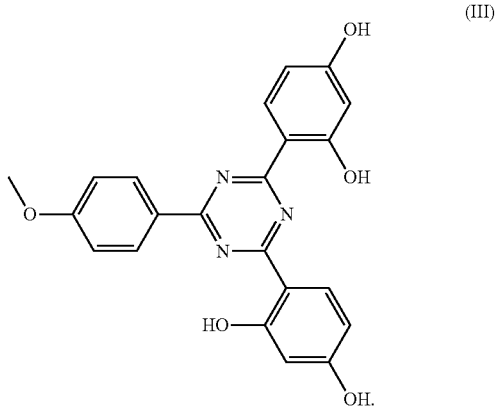 [SMILES: COc1ccc(-c2nc(-c3ccc(O)cc3O)nc(-c3ccc(O)cc3O)n2)cc1]

15. The process according to claim 14, wherein the process further comprises reacting the compound of formula (III) with isooctyl chloride in the presence of a base to obtain a compound of formula (IV)

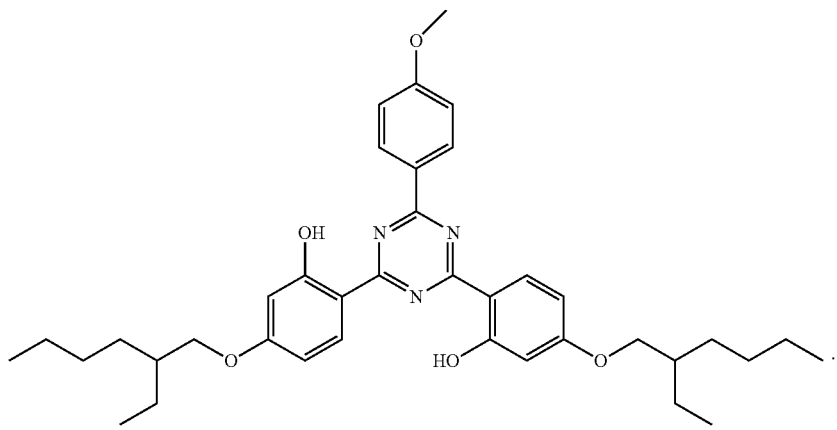

(IV)

16. The process according to claim 8, wherein the solvent is selected from the group consisting of diethylether, tetrahydrofuran, trimethylamine and 1,4-dioxane.

17. The process according to claim 1, wherein in step (i) 4-bromoanisole and magnesium are reacted with each other in a molar ratio of from 1.2:1 to 1:1.2, and wherein in step (ii) the Grignard reagent obtained in step (i) is reacted with the compound of formula (II) in a molar ratio of from 1.2:1 to 1:1.2.

* * * * *